US008722101B2

(12) United States Patent
Tanner-Baumgartner et al.

(10) Patent No.: US 8,722,101 B2
(45) Date of Patent: *May 13, 2014

(54) USE OF IRON(III) COMPLEX COMPOUNDS

(75) Inventors: Jessica Tanner-Baumgartner, St. Gallen (CH); Ranjeet Chandra, Etobicoke (CA); Peter Geisser, St. Gallen (CH)

(73) Assignee: Vifor (International) AG, St. Gallen (CH)

( * ) Notice: Subject to any disclaimer, the term of this patent is extended or adjusted under 35 U.S.C. 154(b) by 83 days.

This patent is subject to a terminal disclaimer.

(21) Appl. No.: 11/815,568

(22) PCT Filed: Jan. 18, 2006

(86) PCT No.: PCT/EP2006/050276
§ 371 (c)(1),
(2), (4) Date: Jan. 3, 2008

(87) PCT Pub. No.: WO2006/084782
PCT Pub. Date: Aug. 17, 2006

(65) Prior Publication Data
US 2008/0214496 A1 Sep. 4, 2008

(30) Foreign Application Priority Data
Feb. 9, 2005 (EP) ..................... 05100907

(51) Int. Cl.
*A61K 33/26* (2006.01)
(52) U.S. Cl.
USPC .......................................... 424/647
(58) Field of Classification Search
CPC ..................................................... A61K 33/26
USPC ......................................................... 424/647
See application file for complete search history.

(56) References Cited

U.S. PATENT DOCUMENTS

| 3,076,798 | A | | 2/1963 | Mueller et al. |
| 3,766,165 | A | | 10/1973 | Rennhard |
| 6,372,715 | B1 | * | 4/2002 | Kaltwasser et al. ............... 514/2 |
| 2003/0044513 | A1 | | 3/2003 | Shah et al. |

FOREIGN PATENT DOCUMENTS

| WO | 95/35113 | | 12/1995 | |
| WO | 02/46241 A2 | | 6/2002 | |
| WO | 03/087164 A1 | | 10/2003 | |
| WO | 2004/037865 A1 | | 5/2004 | |
| WO | WO2004037865 | * | 5/2004 | ........... A61K 31/295 |

OTHER PUBLICATIONS

Singh, K. and Fong, Y.F. and Kuperan, P., European Journal of Haematology, a comparison between intravenous iron polymaltose complex (Ferrum Hausmann(R)) and oral ferrous fumarate in the treatment of iron deficiency anaemia in pregnancy (Feb. 2008), vol. 60, issue 2, pp. 119-124—(abstract only provided).*
Beshara, S. et al., British Journal of Haematology, "Pharmacokinetics and red cell utilization of 52Fe/59Fe-labelled rion polymaltose in anaemic patients using positron emission tomography", Mar. 2003, vol. 120, pp. 853-859.*
Andrews et al., "Disorders of Red Cell Iron During Infancy and Childhood," International Journal of Pediatric Hematology/Oncology, vol. 4, pp. 171-180.
Kolb, "Relation of Iron Supply and Iron Metabolism to Infectious Diseases and Parasitoses and the Competence of the Immune System," Nov. 1, 1988, pp. 597-601, German language.
International Search Report for PCT/EP2006/050276 mailed May 3, 2006, three pages.
Qinghua et al., "Influences of IDA on children's IQ, DQ, physical work capacity and immune function," Journal of Hygiene Research, vol. 23, No. 2, Mar. 1994, pp. 91-94.
English translation of Qinghua et al., "Influences of IDA on children's IQ, DQ, physical work capacity and immune function," three pages.
Devaki, et al., "Effects of Oral Iron (III) Hydroxide Polymaltose Complex Supplementation on Hemoglobin Increase, Cognitive Function, Affective Behavior and Scholastic Performance of Adolescents with Varying Iron Status", Therapeutics for States of Deficiency, (pp. 303-310) eight pages, published 2009.
Devaki, et al., "Effects of Oral Supplementation with Iron (III) Hydroxide Polymaltose Complex on the Hematological Profile of Adolescents with Varying Iron Status", Therapeutics for States of Deficiency, (pp. 389-397), nine pages, published 2008.
Devaki, et al., "Effect of Oral Supplementation with Iron (III)-hydroxide Polymaltose Complex on the Immunological Profile of Adolescents with Varying Iron Status", Iron Polymaltose, (pp. 417-425), nine pages, published 2007.
Chaim Hershko, "Iron Infection and Immune Function", Proceedings of the Nutrition Society (1993) 52, 165-174, ten pages.

* cited by examiner

*Primary Examiner* — Layla Bland
*Assistant Examiner* — Bahar Craigo
(74) *Attorney, Agent, or Firm* — Rankin, Hill & Clark LLP

(57) ABSTRACT

The present invention relates to novel therapeutic uses of iron(III) complex compounds with carbohydrates or derivatives thereof, in the preparation of a medicament for improving immune defence and/or brain performance.

6 Claims, No Drawings

USE OF IRON(III) COMPLEX COMPOUNDS

This application is a United States National Stage filing, under 35 U.S.C. 371, of PCT/EP/2006/050276, filed Feb. 9, 2005, and published as WO 2006/084782 A1, on Aug. 17, 2006, all of which are hereby incorporated herein by reference for all purposes.

The present invention relates to novel therapeutic uses of iron(III) complex compounds with carbohydrates or derivatives thereof, in particular with dextrins or oxidation products of dextrins, in particular in the preparation of medicaments for improving immune defence and/or brain performance.

Iron deficiency is the most frequent trace-element deficiency worldwide. Not only does it affect children, from infants to adolescents, in the developing countries, it is also observed in a significant number of children in the rich, industrialised nations. For example, 28% of teenagers in Canada show signs of iron deficiency.

The use of iron(III) oxide as an active ingredient for the treatment of immune deficiency syndromes, especially AIDS, is known from WO 95/35113.

Therapeutically usable iron injection preparations and processes for their production are known from DE 1467980.

Processes for the preparation of iron(III)-polymaltose complex compounds which are suitable for parenteral administration are known from U.S. Pat. No. 3,076,798.

The use of iron-carbohydrate complexes in the treatment or prophylaxis of iron deficiencies is known from WO 2004037865.

Iron complex compounds with hydrogenated dextrins for the treatment or prophylaxis of iron deficiencies are known from WO 03/087164.

Iron(III)-pullulan complex compounds and their use in the treatment or prophylaxis of iron deficiencies are known from WO 02/46241.

It is known from Baumgartner "New Aspects of Iron Therapy", Second Ferrum Meeting, Lisbon 1994, that both the activity and the cognitive performance of the left hemisphere of the brain are dependent on an individual's iron status. In that publication, Baumgartner mentions a study by Walter, according to which iron-related anaemia significantly leads to restricted mental and psychomotor development in children. The compound used in the study was iron sulfate. However, after administering iron sulfate for 75 days, Walter did not find any improvement in the mental and psychomotor development.

Other studies mentioned in Baumgartner show a significant improvement in cognitive performance with iron therapy.

Baumgartner further presents clinical studies which reflect the influence of the iron status on the immunological functions.

Iron sulfate is known to cause, relatively frequently, unpleasant dose-dependent secondary reactions, such as gastro-intestinal disturbances or discolouration of the teeth. Iron from iron salt compounds is subject to the passive diffusion of free iron ions. The iron can enter the circulation and thereby cause secondary reactions or iron poisoning. Consequently, the $LD_{50}$ value in white mice, at 230 mg of iron/kg, is also relatively low. The use of iron salt compounds is therefore disadvantageous in particular when treating children, in whom iron is particularly important for the development of the brain and the immune system.

The study of Tucker "Iron status and brain function: serum ferritin levels associated with asymmetries of cortical electrophysiology and cognitive performance" (*Am. J. Clin. Nutr.* 1984; 39: 105-113), which is also mentioned in the publication of Baumgartner, shows that brain performance is proportional to the ferritin level.

Oski "Effect of Iron Therapy on Behavior Performance in Nonanemic, Iron-Deficient Infants", PEDIATRICS 1983; Volume 71; 877-880, uses iron dextran. The parenteral use of iron dextran is disadvantageous because a dextran-induced anaphylactic shock can occur.

The inventors therefore set themselves the object of finding readily tolerable iron compounds which are suitable for improving brain performance and immune defence in particular in children, including infants and adolescents.

In a study, they have been able to demonstrate that iron(III) complex compounds with carbohydrates, in particular with polymaltose (maltodextrin), are particularly tolerable, have high patient compliance and bring about a significant improvement in immune defence and/or brain performance. Also surprising was the fact that an early significant improvement in immune defence and/or brain performance is found even though iron(III)-polymaltose complex compounds result in only a slow increase in the ferritin level. On the basis of this result, they completed the present invention. The invention therefore relates to the use of iron(III) complex compounds with carbohydrates or derivatives thereof in the preparation of a medicament for improving immune defence and/or brain performance.

The improvement in immune defence within the scope of the invention means a significant improvement in the immune responses, as is shown, for example, in a significant improvement in the lymphocyte response to phytohaemagglutinin (PHA) using the MTT method, in an improvement in the nitroblue tetrazolium test (MBT) using neutrophils, in an improvement in the bactericidal capacity of neutrophils (PCA) measured by the turbidimetric method, in an improvement in the monoclonal antibodies, for example CD3, CD4, CD8 and CD56, counted, for example, using a BD flow cytometer with a simple staining method, and/or in the antibody response to measles, H. influenza and tetanus.

An improvement in brain performance within the scope of the invention includes in particular an improvement in cognitive functions and emotional behaviour and is expressed, for example, in an improvement in the short-term memory test (STM), in the long-term memory test (LTM), in the Raven progressive matrices test, in the Wechsler adult intelligence scale (WAIS) and/or in the emotional coefficient (Baron EQ-i, YV test; youth version).

Iron(III) complex compounds with carbohydrates which can be used according to the invention preferably include those wherein carbohydrates are selected from the group consisting of dextrans and derivatives thereof, dextrins and derivatives thereof and also pullulan, oligomers and/or derivatives thereof. Particular preference is given to iron(III) complex compounds with dextrins or oxidation products thereof. Examples of the preparation of the iron(III) complex compounds according to the invention are found, for example, in patent specifications DE 14679800, WO 04037865 A1, U.S. Pat. No. 3,076,798, WO 03/087164 and WO 02/46241 mentioned at the beginning, the totality of the disclosures of which, in particular in respect of the preparation processes, is to be incorporated herein. The term "dextrins", which are preferably used according to the invention, is a collective term for various lower and higher polymers of D-glucose units, which form during the incomplete hydrolysis of starch. They can also be prepared by polymerisation of sugars (e.g. WO02083739 A2, US20030044513 A1, U.S. Pat. No. 3,766,165). The dextrins include the maltodextrins, or polymaltoses, which are prepared by enzymatic cleavage of maize or potato starch with alpha-amylase and which are characterised by the degree of hydrolysis, expressed by the DE value (dextrose equivalent). Polymaltose can also be obtained according to the invention by acid hydrolysis of dextrins. The preparation of the iron(III) complex compounds which can be used according to the invention is generally carried out by reacting iron(II) or iron(III) salts, in particular iron(III) chloride, with the dextrins, in particular polymaltose, or oxidation products of the dextrins in aqueous alkaline solution (pH>7) and then working up. Preparation in the weakly acidic pH range is also possible. However, alkaline pH values of, for example, >10 are preferred.

The pH value is preferably increased slowly, or gradually, which can be achieved, for example, by first adding a weak base, for example to a pH of about 3; further neutralisation can then be carried out with a stronger base. There are suitable as the weak base, for example, alkali or alkaline earth carbonates and bicarbonates, such as sodium and potassium carbonate or bicarbonate, or ammonia. Examples of strong bases include alkali or alkaline earth hydroxides, such as sodium, potassium, calcium or magnesium hydroxide.

The reaction can be promoted by heating. For example, temperatures in the order of magnitude of from 15° C. to the boiling point can be used. It is preferred to increase the temperature gradually. For example, heating to about 15 to 70° C. can be carried out first, and then the temperature can gradually be increased to boiling.

The reaction times are, for example, in the order of magnitude of from 15 minutes to several hours, e.g. from 20 minutes to 4 hours, for example from 25 to 70 minutes, e.g. from 30 to 60 minutes.

When the reaction has taken place, the resulting solution can be cooled to room temperature, for example, and optionally diluted and optionally filtered. After cooling, the pH value can be adjusted to the neutral point or slightly below, for example to values of from 5 to 7, by addition of acid or base. Examples of bases which may be mentioned include those mentioned above for the reaction. Acids include, for example, hydrochloric acid and sulfuric acid. The resulting solutions are purified and can be used directly in the preparation of medicaments. However, it is also possible to isolate the iron (III) complexes from the solution, for example by precipitation with an alcohol, such as an alkanol, for example ethanol. The isolation can also be carried out by spray-drying. Purification can be carried out in the conventional manner, in particular for the removal of salts. This can be effected, for example, by reverse osmosis, it being possible for such a reverse osmosis to be carried out, for example, before the spray-drying or before the product is used directly in medicaments.

The resulting iron(III) complexes have, for example, an iron content of from 10 to 40% wt./wt., in particular from 20 to 35% wt./wt. They are generally readily soluble in water. It is possible to prepare therefrom neutral aqueous solutions having an iron content of, for example, from 1% wt./vol. to 10% wt./vol. Such solutions can be thermally sterilised.

Regarding the preparation of iron(III)-polymaltose complex compounds, reference may be made to U.S. Pat. No. 3,076,798.

In a preferred embodiment of the invention, an iron(III) hydroxide-polymaltose complex compound is used. The iron (III)-polymaltose complex compound preferably has a molecular weight in the range from 20,000 to 500,000 daltons, in a preferred embodiment from 30,000 to 80,000 daltons (determined by means of gel permeation chromatography, for example as described by Geisser et al. in Arzneim. Forsch/Drug Res. 42(11), 12, 1439-1452 (1992), paragraph 2.2.5). A particularly preferred iron(III) hydroxide-polymaltose complex compound is Maltofer® from Vifor AG, Switzerland, which is available commercially. In a further preferred embodiment, an iron(III) complex compound with an oxidation product of one or more maltodextrins is used. This is obtainable, for example, from an aqueous iron(III) salt solution and an aqueous solution of the product of the oxidation of one or more maltodextrins with an aqueous hypochlorite solution at a pH value in the alkaline range, wherein when a maltodextrin whose dextrose equivalent is from 5 to 37 is used and when a mixture of a plurality of maltodextrins is used, the dextrose equivalent of the mixture is from 5 to 37 and the dextrose equivalent of the individual maltodextrins contained in the mixture is from 2 to 40. The weight-average molecular weight Mw of the complexes so obtained is, for example, from 30 kDa to 500 kDa, preferably from 80 to 350 kDa, particularly preferably up to 300 kDa (determined by means of gel permeation chromatography, for example as described by Geisser et al. in Arzneim. Forsch/Drug Res. 42(11), 12, 1439-1452 (1992), paragraph 2.2.5). Reference may be made in this connection to WO 2004037865 A1, for example, the totality of the disclosure of which is to be incorporated in the present application.

Regarding the preparation of iron complex compounds with hydrogenated dextrins, reference may be made to WO 03/087164.

Regarding the preparation of iron(III)-pullulan complex compounds, reference may be made to WO 02/46241.

The iron(III) hydroxide complex compounds used according to the invention are preferably administered orally. In principle, however, they can also be administered parenterally, such as intravenously, or intramuscularly. The daily oral dose is, for example, from 10 to 500 mg of iron/day of use. Administration can continue, without hesitation, over a period of several months until there is an improvement in the patient's iron status, reflected by the haemoglobin value, the transferrin saturation and the ferritin value. Oral administration preferably takes place in the form of a tablet, a capsule, an aqueous solution or emulsion, in the form of granules, a capsule, a gel or in the form of a sachet. Solutions or emulsions are preferably administered, in particular to children, in the form of syrups or juices, drops, etc. To this end, the iron(III) hydroxide-dextrin complex compounds can be brought into the suitable form of administration with conventional pharmaceutical carriers and auxiliary substances. To this end, conventional binders or glidants, diluents, disintegrators, etc. can be used.

The use according to the invention can take place in children, young people and adults. It preferably takes place for the preparation of a medicament for treating children. Children include infants and adolescents or young people.

The use according to the invention proceeds in particular by improving the neutrophil level, the antibody level and/or the lymphocyte function, determined, for example, by the lymphocyte reaction to phytohaemagglutinin.

The use according to the invention can serve to treat patients with iron deficiency anaemia, iron deficiency without anaemia as well as patients without iron deficiency anaemia or iron deficiency, preferably for treating patients with iron deficiency. This classification is dependent on the age and sex of the patient and can also vary from person to person. Classification can be made, for example, by the haemoglobin value and the value for transferrin saturation (%). Reference values for haemoglobin, determined by flow cytometry (photometric): cyan-haemoglobin method, are listed, for example, in Charite, Institut für Laboratoriumsmedizin und Pathobiochemie (http://www.charite.de/ilp/routine/parameter.html). Transferrin saturation in patients without iron deficiency is generally >16%.

According to M. Wick, W. Pinggera, P. Lehmann, Eisenstoffwechsel—Diagnostik und Therapien der Anämien, 4., enlarged edition, Springer Verlag Vienna 1998, all forms of iron deficiency can be detected clinico-chemically. A reduced ferritin concentration is generally accompanied, by way of compensation, by increased transferrin and low transferrin saturation.

Surprisingly, improvements in immune defence and/or brain performance have also been achieved according to the invention in patients who had a normal haematological result in respect of iron status.

The mode of action of the invention is explained and demonstrated by the example which follows.

EXAMPLE

Using a film-coated tablet (620 mg per tablet) containing 357.0 mg of an iron(III) hydroxide-polymaltose complex compound (Maltofer®), corresponding to 100 mg of iron, a single-centre study of oral iron supplementation in adolescents with iron deficiency, with or without anaemia, in comparison with a placebo group was carried out.

The aim of the comparative study was to study the effects of orally administered iron(III) hydroxide-polymaltose complex (100 mg of iron per day and placebo for 6 days per week for 8 months) on the immune responses, the haematological status, the cognitive functions and the behavioural functions in four groups of adolescents with iron deficiency anaemia, with iron deficiency, without iron deficiency and anaemia (iron supplementation) and a further group without iron deficiency and anaemia (placebo group).

To this end, 500 apparently healthy adolescents of both sexes aged between 15 and 18 were chosen at random and divided into the following groups using a plurality of haematological criteria.

| Group | Haemoglobin (g/dl) | Transferrin saturation (%) |
|---|---|---|
| A: iron deficiency anaemia (IDA) | boys: 7-<11.5 girls: 7-<10.5 | <16 <16 |
| B: iron deficiency (ID) | boys: ≥11.5 girls: ≥10.5 | <16 <16 |
| C: no iron deficiency, no anaemia, normal supplementation (NS) | boys: ≥11.5 girls: ≥10.5 | ≥16 ≥16 |
| D: placebo, no anaemia, normal placebo (NP) | boys: ≥11.5 girls: ≥10.5 | ≥16 ≥16 |

Each group consisted of 30 test subjects and there was a total of 120 test subjects, who were divided into the above-mentioned four groups (NP, NS, ID and IDA).

Test Process:

Haematological Evaluation:

Venous blood was taken from all 120 test subjects using vacuum test tubes, and all the blood parameters were analysed in a Sysmax blood test. The serums were separated from the blood samples and stored at −20° C. Serum samples were subjected to SFe and TIBC determinations by standard methods (NIN-Manual 1983). TS was calculated from SFe and TIBC and given as a percentage. Serum ferritin analyses were carried out using an "enzyme linked immuno sorbent assay" (ELISA).

Serum folate and cyanacobalamin (B12) were determined by standard methods.

Immune Responses:

Neutrophils and lymphocytes were separated from fresh blood samples by the single-stage double density gradient method, and the following immunological assays were carried out for all 120 test subjects:
lymphocyte response to phytohaemagglutinin (PHA) using the MTT method;
nitroblue tetrazolium test (MBT) using neutrophils;
bactericidal capacity of the neutrophils (BCA) measured by the turbidimetric method.

Using fresh samples of whole blood, counts of the monoclonal antibodies CD3, CD4, CD8 and CD56 were carried out using a BD flow cytometer by the single-staining method and expressed as a percentage for all 120 subjects. The following tests were carried out using serum samples from all 120 test subjects:
antibody responses to measles, flu viruses and tetanus;
C-reactive protein using a semi-quantitative method.

Cognitive Functions and Emotional Behaviour

The cognitive functions and the emotional behaviour of the 120 test subjects were determined in accordance with the most frequently used tests and according to established methods:
1. short-term memory test (STM)
2. long-term memory test (LTM)
3. Raven progressive matrices (RPM)
4. Wechsler adult intelligence scale (WAIS)
5. emotional quotient (Baron EQ-i; YV test; youth version).

Evaluation of Achievement in School

The achievements of the 120 test subjects in school were determined individually by means of a school achievement test.

Anthropometric evaluations, physical examinations, urine and stool examinations were carried out by standard methods.

Statistical Evaluation:

Comparison of the average values of the parameters over successive time periods gave a picture of the effect of the treatment. The nature of the evaluation meant that a repeated measures design was required. For each parameter there were three sets of observations, which were all correlated. Consequently, the repeated measures test is the suitable means, and the statistical analysis was carried out using SPSS software. The method tests the significance of the parameter values over the duration (points of time) between the groups and, if present, interaction between duration and group. Multiple comparisons between different groups were carried out automatically by the repeated measures test with the aid of LSD (least significance difference test).

Results

Advantageous effects were found in all the tests carried out, namely in respect of the haematological status, the immune status, the cognitive function and the emotional behaviour.

Significant increments were found for all iron-related haematological parameters from the baseline to four months and again from four months to eight months of the supplementation in all groups to which the iron preparation was given, namely the group with iron deficiency with (IDA) or without (ID) anaemia and the group with normal haematology which received supplementation (NS).

There was a significant increase in the lymphocyte response to phytohaemagglutinin, bacterial killing by neutrophil assay, nitroblue tetrazolium test and the levels of antibodies towards measles and Haemophilus influenza in the three groups with supplementation (IDA, ID, NS) for the periods 0 to 4 months and 4 to 8 months. For antibodies to tetanus, the difference between the baseline and 8 months was significant for these three groups.

The cognitive performance improved from the baseline to four months and from 4 to 8 months in all the tests, including SAT, with the exception of EQ.

These increments in haematological, immunological and cognitive functions have important clinical significance. By the regular administration of an iron(III) hydroxide-polymaltose complex, immune defence and brain performance can be improved, with enormous advantages to society.

The invention claimed is:

1. A method of increasing at least one of a neutrophil level, an antibody level, and a lymphocyte function as measured by a lymphocyte reaction to phytohemoglobin in a human patient, the method consisting of administering to a human patient not having iron deficiency anemia or iron deficiency a medication consisting of an iron (III) compound selected from the group consisting of iron (III) polymaltose and an iron (III) maltodextrin complex, the iron (III) maltodextrin complex comprising a complex of an oxidation product of one or more maltodextrins with iron (III), relative to a human patient not so administered.

2. A method of improving an immune defense in a human patient consisting of administering to a human patient not having an iron deficiency anemia or an iron deficiency a medication consisting of an iron (III) compound selected from the group consisting of iron (III) polymaltose and an iron (III) maltodextrin complex, the iron (III) maltodextrin complex comprising a complex of an oxidation product of one or more maltodextrins with iron (III), wherein the human patient may be of any age.

3. The method of claim 1, wherein the iron (III) polymaltose complex has a molecular weight ($M_w$) of 20,000 to 500,000 Daltons.

4. The method of claim 1, wherein the iron (III) polymaltose complex has a molecular weight (Mw) of 30,000 to 80,000 Daltons.

5. The method of claim 2, wherein the iron (III) polymaltose complex has a molecular weight ($M_w$) of 20,000 to 500,000 Daltons.

6. The method of claim 2, wherein the iron (III) polymaltose complex has a molecular weight (Mw) of 30,000 to 80,000 Daltons.

* * * * *